United States Patent
Busch et al.

(10) Patent No.: US 7,412,286 B2
(45) Date of Patent: Aug. 12, 2008

(54) BIATRIAL TRIPLE-CHAMBER CARDIAC PACEMAKER WITH MULTI-CONDITIONAL INHIBITION OF SECOND ATRIAL STIMULATION

(75) Inventors: Ulrich Busch, Berlin (DE); Max Schaldach, deceased, late of Erlangen (DE); by Max Schaldach, Jr., legal representative, Berlin (DE)

(73) Assignee: Biotronik GmbH & Co. KG, Berlin (DE)

( * ) Notice: Subject to any disclaimer, the term of this patent is extended or adjusted under 35 U.S.C. 154(b) by 871 days.

(21) Appl. No.: 10/652,861

(22) Filed: Aug. 29, 2003

(65) Prior Publication Data
US 2004/0172073 A1 Sep. 2, 2004

(30) Foreign Application Priority Data
Sep. 2, 2002 (DE) ................................. 102 41 089

(51) Int. Cl.
*A61N 1/368* (2006.01)
(52) U.S. Cl. ............................................................ 607/9
(58) Field of Classification Search .................. 607/9, 607/18
See application file for complete search history.

(56) References Cited

U.S. PATENT DOCUMENTS

| 4,825,870 | A | | 5/1989 | Mann | |
|---|---|---|---|---|---|
| 5,514,161 | A | | 5/1996 | Limousin | |
| 5,584,867 | A | | 12/1996 | Limousin | |
| 5,776,167 | A | | 7/1998 | Levine | |
| 5,902,324 | A | * | 5/1999 | Thompson et al. | 607/9 |
| 6,128,532 | A | | 10/2000 | Stoop | |
| 6,249,701 | B1 | | 6/2001 | Rajasekhar | |
| 6,553,258 | B2 | * | 4/2003 | Stahmann et al. | 607/9 |
| 2002/0082653 | A1 | * | 6/2002 | Stahmann et al. | 607/9 |
| 2002/0183792 | A1 | * | 12/2002 | Struble | 607/9 |
| 2002/0183795 | A1 | * | 12/2002 | Rouw et al. | 607/9 |
| 2003/0199931 | A1 | * | 10/2003 | Stahmann et al. | 607/9 |

\* cited by examiner

*Primary Examiner*—George Manuel
*Assistant Examiner*—Christopher A Flory
(74) *Attorney, Agent, or Firm*—David J. Muzilla; Hahn Loeser & Parks, LLP

(57) ABSTRACT

A biatrial triple-chamber cardiac pacemaker has at least one sensing unit for sense events of a first atrium and a ventricle of a heart and at least one stimulation unit which is adapted to produce stimulation pulses to a second atrium and the ventricle, and a control which is connected to the sensing unit and the stimulation unit and is adapted to evaluate at least the atrial sense events ($A_R$-Sense) associated with the first atrium and the ventricular sense events (V-Sense) associated with the ventricle, for actuation of the stimulation unit, which is actuated so that the delivery of a left-atrial stimulation pulse is suppressed if previously a ventricular sense event occurs in a crosstalk window which adjoins a postatrial ventricular blanking time and at the same time the distance in respect of time to the last ventricular event ascertained outside a crosstalk window, to the next possible ventricular stimulation event, is greater than a predetermined maximum value.

16 Claims, 2 Drawing Sheets

BIATRIAL TRIPLE-CHAMBER CARDIAC PACEMAKER WITH MULTI-CONDITIONAL INHIBITION OF SECOND ATRIAL STIMULATION

The invention concerns a biatrial triple-chamber cardiac pacemaker comprising at least one sensing unit (e.g., $A_{LS}$, $V_S$, and $A_{RS}$ of FIG. 1) for detecting signals related to a natural contraction of an atrium and a ventricle of a heart and at least one stimulation unit which is adapted to produce stimulation pulses for the stimulation of a second atrium and the ventricle of the heart. The cardiac pacemaker further includes a control which is connected to the sensing unit and the stimulation unit and which is adapted to evaluate at least the atrial sense events associated with the first atrium and the ventricular sense events associated with the ventricle, for actuation of the stimulation unit. Actuation is effected having regard to a ventricular escape interval and possibly a postatrial ventricular blanking time in such a way that a right-atrial sense event triggers the ventricular escape interval, at the end of which a ventricular stimulation pulse is triggered if same is not inhibited by a ventricular sense event within the ventricular escape interval and possibly outside the postatrial ventricular blanking time. Actuation is further effected having regard to an interatrial conduction time in such a way that a right-atrial sense event triggers the interatrial conduction time, at the end of which a left-atrial stimulation pulse is triggered which is possibly inhibited by a left-atrial sense event within the atrial conduction time.

BACKGROUND OF THE ART

Triple-chamber cardiac pacemakers of that kind are known, for example, from U.S. Pat. Nos. 5,514,161 and 5,584,867. These patents provide structures with which it is possible to prevent conduction of an atrial tachycardia to the ventricle of a heart by means of the cardiac pacemaker.

Many of the per se known dual- and triple-chamber cardiac pacemakers are so-called demand cardiac pacemakers which are so designed that stimulation pulses to a chamber of a heart are triggered only if no natural heart action is detected within a predetermined time window. In connection with ventricular cardiac pacemakers for example reference is made to a ventricular escape interval or an AV-time which is triggered with a stimulation or a natural event in the right atrium of the heart and at the end of which a ventricular stimulation pulse is produced if that is not inhibited because, during the ventricular escape interval, an event was detected in the heart ventricle to be stimulated.

Such a detected event (V-sense) can be caused by a natural contraction of the ventricle. Similar electrical signals as occur upon the natural contraction of a ventricle can however also be produced by crosstalk of signals produced in the atrium of a heart, for example an atrial stimulation, to the ventricle. In order to blank out the detection of such signals originating from the atrium in the ventricle pacemakers usually have a blanking time which is triggered for example with the application of a stimulation pulse to the right atrium of a heart and lasts for example 100 ms. During that blanking time no ventricular sense events are detected so that potentials which possibly occur in that blanking time in the ventricle do not result in inhibition of the delivery of a ventricular stimulation pulse.

In general terms there is a wish for the blanking time to be selected to be as short as possible in order more specifically to prevent crosstalk of atrial stimulation pulses into the sensing channel for ventricular events, but at the same time to detect natural ventricular events, in particular premature ventricular contractions (PVC). Detecting and taking account of such premature ventricular contractions is also desirable for the reason that they can suppress the delivery of a ventricular stimulation pulse. Otherwise, in the worst case scenario, a ventricular stimulation pulse could be triggered in such a way that it occurs in the so-called vulnerable phase after a ventricular contraction.

The above-outlined problems are countered in various different ways in dual-chamber cardiac pacemakers. Reference may be made here to U.S. Pat. Nos. 5,776,167 and 4,825,870. The cardiac pacemaker in accordance with U.S. Pat. No. 4,825,870 counters the above-outlined problems by the provision of a variable blanking time and a subsequent crosstalk window, during which ventricular events are detected and identified as crosstalk events.

The state of the art does not indicate hitherto that, in the case of a triple-chamber cardiac pacemaker, crosstalk on the basis of atrial stimulation can be attributed not only to stimulation of the right atrium (as is known in the case of dual-chamber cardiac pacemakers) but stimulation of the left atrium. The invention already starts with the realisation that stimulation of the left atrium occurs in respect of time after stimulation of the right atrium, more specifically after an atrial conduction time, so that crosstalk from the left atrium to the (right) ventricle can only occur markedly after the crosstalk of a right-atrial stimulation pulse.

SUMMARY OF THE INVENTION

The invention counters that problem with a cardiac pacemaker of the kind set forth in the opening part of this specification, in which actuation is effected in such a way that the delivery of an atrial stimulation pulse is suppressed if either previously a ventricular sense event occurs in a crosstalk window which adjoins the postatrial ventricular blanking time and at the same time the distance in respect of time to the last ventricular event ascertained outside a crosstalk window, to the next possible ventricular stimulation event, is greater than a predetermined maximum value and/or a ventricular sense event occurs during a UTI (upper tracking interval) operating mode in which the cardiac pacemaker works at a predetermined maximum stimulation rate (UTR=upper tracking rate).

In summary the way of resolving the problem which is recognised in accordance with the invention is that of entirely preventing the delivery of a left-atrial stimulation pulse and therewith also the possibility of crosstalk of such a stimulation pulse to the ventricular sensing channel if a ventricular event could be attributed to crosstalk because of left-atrial stimulation.

As such a crosstalk effect, precisely like a natural ventricular contraction, would have to result in inhibition of the ventricular stimulation pulse, in the worst case scenario the ventricular stimulation could be suppressed so long that this is physiologically disadvantageous.

In the first variant therefore the delivery of a left-atrial stimulation pulse is always suppressed precisely when corresponding crosstalk perception would result in a ventricular rate (identified by longer than a predetermined maximum VV-interval), which is physiologically questionable.

In specific terms a timer measures the respective time which has elapsed since the last secured ventricular event—irrespective of whether the last ventricular event represents a natural contraction or a stimulation—and adds to that time the time which still passes to the next planned ventricular stimulation pulse. There is a VV-interval. If that currently calculated VV-interval is greater than a predetermined maximum interval, the next following left-atrial stimulation is suppressed in order to prevent with certainty far-field perception of the corresponding, left-atrial stimulation pulse, and inhibition, caused thereby, of the next ventricular stimulation pulse. Inhibition of the next planned ventricular stimulation pulse on the basis of a natural ventricular contraction is then always still possible, but on the basis of inhibition of the left-atrial stimulation pulse inhibition cannot be due to far-field perception of such a stimulation pulse.

The alternative variant takes account of the fact in particular that, in cardiac pacemakers, an upper limit for the stimulation frequency is usually predetermined. If a perceived atrial rate exceeds that upper limit in terms of stimulation frequency, stimulation of the ventricle can no longer take place in atrium-synchronous relationship. In so-called mode switching the cardiac pacemaker then switches over to an asynchronous stimulation mode which involves an upper tracking rate. By virtue of asynchronicity of atrial and ventricular events that affords inhibition of a ventricular stimulation pulse on the basis of far-field perception of a left-atrial stimulation pulse. Left-atrial stimulation is therefore switched off when the pacemaker works in an operating mode at the greatest predetermined ventricular stimulation frequency.

BRIEF DESCRIPTION OF THE DRAWINGS

The invention will now be described in greater detail by means of an embodiment with reference to the drawings in which.

DETAILED DESCRIPTION OF A PREFERRED EMBODIMENT

Figure 1:
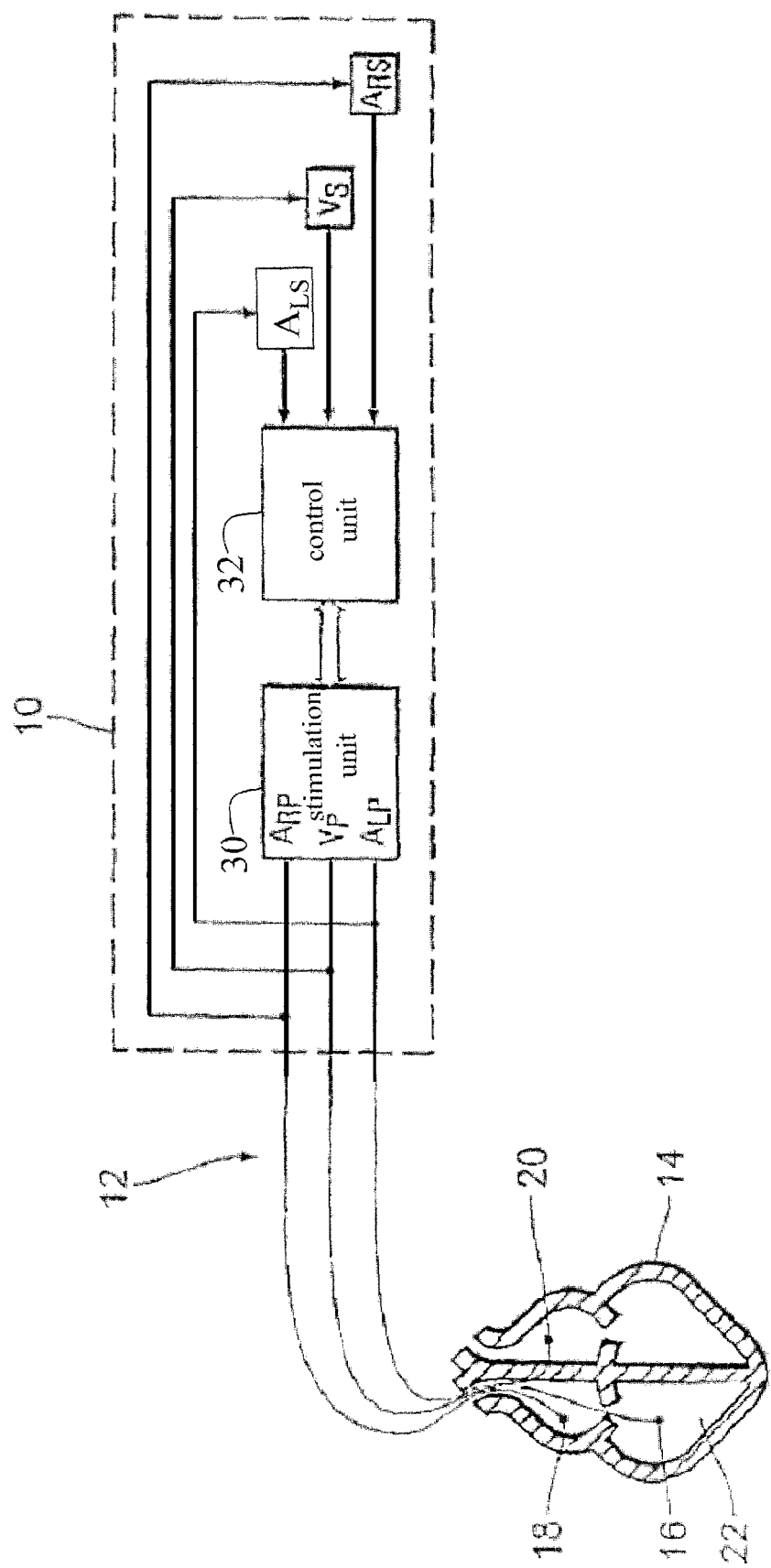
FIG. 1 is a view showing the principle of a dual-chamber cardiac pacemaker.

Usually a cardiac pacemaker as is indicated by reference numeral 10 in FIG. 1 is connected to an electrode line 12 which leads into a human heart 14. In the case of a triple-chamber cardiac pacemaker, like that shown in FIG. 1, stimulation and/or sensing electrodes 16 through 20 are so placed in the heart 14 that the electrode 16 picks up electrical potentials in the left ventricle 22 of the heart 14 and can deliver stimulation pulses to the left ventricle 22. The electrode 16 can be of a unipolar or bipolar nature. In the first-mentioned unipolar case the electrode line 12, at its distal end leading into the left ventricle, has a single electrically conductive surface. Alternatively it is also possible to provide two or more electrically conductive surfaces which make it possible to record potentials in the left ventricle between two electrically conductive surfaces or correspondingly deliver stimulation pulses. In the unipolar case a housing of the cardiac pacemaker 10 forms the respective counterpart pole for the ventricular electrode 16.

Corresponding considerations apply in respect of the right-atrial electrode 18 placed in the right atrium and the left-atrial electrode 20 placed in the left atrium. Those electrodes can also be of a unipolar or bipolar nature. Electrode lines which permit corresponding placement of the electrodes in the right ventricle, the right atrium and the left atrium are basically known.

The electrodes 16 through 20 are each connected by way of respective separate electric lines of the electrode line 12 to the cardiac pacemaker 10. It is also conceivable that, instead of separate electric lines in the electrode line 12 fewer electric lines than electrode surfaces are provided, which then for example, in a multiplexing process, pass electrical potentials recorded by the electrodes in the heart, in the form of signals, to the cardiac pacemaker, or conversely pass stimulation pulses from the cardiac pacemaker to the heart.

The cardiac pacemaker 10 is designed in such a way that it can deliver electrical stimulation pulses selectively and controlledly, by means of a stimulation unit 10, by way of the electrode line 12 and one or more of the electrodes 16 through 20 to the corresponding chamber of the heart 14. In the case of a pure pacemaker mode which serves for properly timed stimulation of the individual chamber for need-related blood supply for a patient, only a respective one of the chambers is stimulated at a respective moment in time.

For appropriate actuation the stimulation unit 30 is connected to a control unit 32 which provides for such need-related actuation of the stimulation unit 30 and accordingly stimulation pulse delivery to one of the chambers of the heart 14.

Stimulation of a respective chamber should result in contraction of the respective chamber. The production of correspondingly appropriate stimulation pulses and also monitoring of the stimulation outcome are also basically known.

The time sequence of the stimulation pulses is so selected as to afford a time sequence of the contractions of the chambers of the heart, as occurs in a natural fashion in a healthy heart. A contraction of the right atrium is followed by a contraction of the right ventricle after an atrio-ventricular conduction time (AV-conduction time). Contraction of the left atrium also takes place in time-displaced relationship, starting from a contraction of the right atrium, after an interatrial conduction time (AA-conduction time).

Contraction of the right ventricle is followed in turn by contraction of the right atrium, after a VA-time. Contraction of the individual chambers of the heart involves depolarisation of the cardiac tissue (myocardium), which leads to measurable electrical potentials. In response to depolarisation and contraction of the myocardium repolarisation occurs, after which the myocardium is ready for a fresh contraction.

The control unit 32 is therefore designed in such a way that it starts an AA-interval timer in response to a detected natural event in the right atrium ($A_R$-Sense), if, within the $A_R A_L$-time predetermined by that timer, a natural contraction of the left atrium is detected ($A_L$-Sense) stimulation of the left atrium ($A_L$-Pace) is inhibited at the end of the $A_R A_L$-time. If no $A_L$-Sense is detected during the $A_R A_L$-time, a left-atrial stimulation pulse is delivered at the end of the $A_R A_L$-time; see FIG. 2.

With a right-atrial event, whether it is the detection of a natural right-atrial contraction ($A_R$-Sense) or the delivery of a right-atrial stimulation pulse ($A_R$-Pace), a ventricular escape interval is triggered, at the end of which a (right-)ventricular stimulation pulse (V-Pace) is delivered if, within the escape interval, no natural contraction of the ventricle (V-Sense) is detected. If an electrical potential possibly characterising a ventricular contraction is detected within the escape interval the ventricular stimulation pulse (V-Pace) is inhibited at the end of the escape interval (see FIG. 2). In the case of a rate-controlled pacemaker the duration of the escape interval generally depends on a measurement value characterising the physiological demand of a patient.

The right-atrial event ($A_R$-Sense or $A_R$-Pace) not only triggers the ventricular escape interval (also referred to as the AV-delay) but also initially a blanking value of for example a hundred milliseconds in duration, within which the control 32 does not detect ventricular sense events (V-Sense), or at least does not process same. In the former case reference is made to the absolute refractory time of the pacemaker while in the latter case reference is made to the relative refractory time. As explained in the opening part of this specification the purpose of the blanking interval is to blank out far-field perception of a stimulation pulse for the right atrium in the right ventricle so that such a potential which is due to the far-field effect is not detected in the right ventricle and leads to inhibition of a ventricular stimulation pulse.

Figure 2:
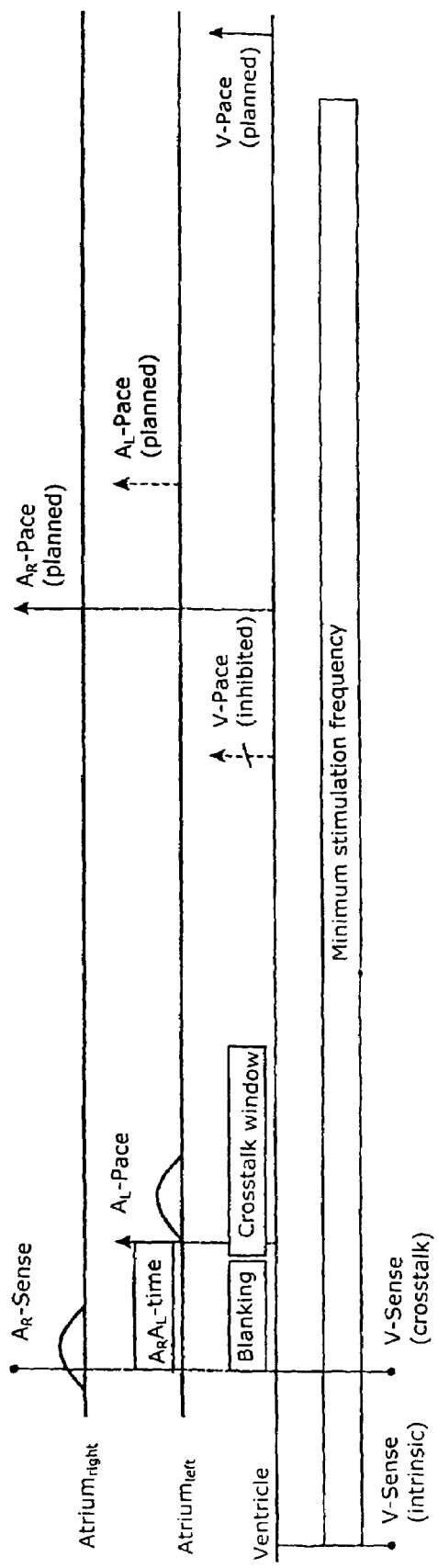
FIG. 2 shows a time chart in respect of the control of a cardiac pacemaker as shown in FIG. 1.

The triple-chamber pacemaker shown in FIG. 1 further entails the possibility of also stimulating the left atrium. FIG. 2 shows the delivery of a left-atrial stimulation pulse ($A_L$-Pace) after the expiry of the $A_R A_L$-time. The left-atrial stimulation pulse can also lead by means of far-field perception to a ventricular sense event (V-Sense) as is also shown by a broken line in FIG. 2. That perception is outside the blanking time and therefore leads to inhibition of the ventricular stimulation pulse (V-Pace) which is otherwise delivered at the end of the ventricular escape interval. The background here is that a premature natural contraction of the ventricle (PVC=premature ventricular contraction) should in fact result in inhibition of the ventricular stimulation pulse. By virtue of inhibition of the ventricular stimulation pulse, because of the far-field perception of the left-atrial stimulation pulse, the next ventricular stimulation pulse can occur at the earliest after the expiry of a further ventricular escape interval which is triggered by a right-atrial event which after a VA-time follows the inhibited ventricular stimulation pulse. The next ventricular stimulation pulse which is already timed (identified in FIG. 2 as V-Pace (planned)) could also again be inhibited in the case of a conventional triple-chamber pacemaker by a left-atrial stimulation pulse. In that way it can happen that the ventricle is not stimulated for some periods and in that time possibly also does not contract in a natural fashion.

Therefore the control unit of the triple-chamber pacemaker according to the invention as described herein is designed in such a way that, with the last secure ventricular event—whether it is an intrinsic natural event or also a stimulated event—, a time counter is started and the procedure involves regularly comparing whether the time from the last secure ventricular event to the next planned event exceeds a predetermined maximum. That predetermined maximum is preferably stored in a non-volatile memory of the cardiac pacemaker and can either be predetermined by a doctor or however can also be self-adjustingly set.

In addition the control unit 32 is designed in such a way that it takes account of a crosstalk window that begins with the end of the blanking time after a right-atrial event and in the case of ventricular events—such as for example far-field perception of the left-atrial stimulation pulse—within the crosstalk window checks whether the next planned ventricular stimulation pulse would result in a maximum VV-period being exceeded as described hereinbefore (that corresponds to a minimum stimulation frequency). If the two conditions, namely on the one hand a ventricular event in the crosstalk window and on the other hand the fact that a maximum VV-period is possibly exceeded, are satisfied, the control unit 32, with the next following right-atrial event, does not trigger the interatrial conduction time ($A_R A_L$-time), at the end of which a left-atrial stimulation pulse would be delivered. De facto the control unit switches over the triple-chamber pacemaker to a dual-chamber mode. This ensures that no left-atrial stimulation pulse is delivered, which would implement inhibition of a ventricular stimulation pulse, with the consequence that the resulting VV-interval exceeds the predetermined maximum duration.

In a simplified embodiment an alternative control unit 32 is so designed that the interatrial synchronisation is switched off—that is to say switching over to the dual-chamber mode takes place—whenever a ventricular sense event is detected, during which the cardiac pacemaker is in an operating mode in which it is working at a maximum predetermined stimulation rate (upper tracking rate). In that case stimulation of the ventricle is no longer controlled by atrial events as those atrial events would result in an excessively high ventricular rate. In the fashion of the per se known mode switching the alternative control unit 32 switches the cardiac pacemaker from the atrium-synchronous mode into an asynchronous mode in which the ventricle is stimulated at the maximum stimulation rate. On the basis of that asynchronicity left-atrial stimulation pulses, after the expiry of an intraatrial conduction time could easily result by means of far-field perception in ventricular sense events which are not due to a natural contraction of the ventricle. That could involve the above-described, longer-duration suppression of stimulation of the ventricle. Therefore, the alternative stimulation unit 32 is so designed that it switches off interatrial synchronisation in the case of a ventricular sense event in the upper tracking rate mode.

The invention claimed is:

1. A biatrial triple-chamber pacemaker for use with a heart having a first and a second atrium and a first and a second ventricle, said pacemaker comprising:
  at least one sensing unit for sense events of the first atrium and the first ventricle;
  at least one stimulation unit which is adapted to produce stimulation pulses to the second atrium and the first ventricle; and
  a control unit which is connected to the sensing unit and the stimulation unit and which is adapted to evaluate, for actuating the stimulation unit, at least the atrial sense events ($A_R$-Sense) associated with the first atrium and the ventricular sense events (V-Sense) associated with the first ventricle;
  wherein the stimulation unit is actuated with regard to a ventricular escape interval and a postatrial ventricular blanking time such that an occurrence of the atrial sense event ($A_R$-Sense) triggers the ventricular escape interval, at the end of which a ventricular stimulation pulse is triggered if same is not inhibited by an occurrence of the ventricular sense event within the ventricular escape interval and outside the postatrial ventricular blanking time,
  wherein the stimulation unit is actuated with regard to an interatrial conduction time such that an occurrence of the atrial sense event ($A_R$-Sense) triggers an interatrial conduction timer to create a predetermined $A_R$-$A_L$ time interval, at the end of which a stimulation pulse to the second atrium is triggered if the stimulation pulse to the second atrium is not inhibited, and
  wherein the stimulation unit is actuated such that the delivery of a stimulation pulse to the second atrium is suppressed when previously an occurrence of the ventricular sense event occurs in a crosstalk window which adjoins a postatrial ventricular blanking time and at the same time a time interval, between a last ventricular sensed event occurring outside the crosstalk window and a next possible (scheduled) ventricular stimulation event, is greater than a predetermined maximum value.

2. A biatrial triple-chamber cardiac pacemaker for use with a heart having a first and a second atrium and a first and a second ventricle, said pacemaker comprising:

at least one sensing unit for sense events of the first atrium and the first ventricle;

at least one stimulation unit which is adapted to produce stimulation pulses to the second atrium and the first ventricle; and a control unit which is connected to the sensing unit and the stimulation unit and which is adapted to evaluate, for actuating the stimulation unit, at least the atrial sense events ($A_R$-Sense) associated with the first atrium and the ventricular sense events (V-Sense) associated with the first ventricle;

wherein the stimulation unit is actuated with regard to a ventricular escape interval and a postatrial ventricular blanking time such that an occurrence of the atrial sense event ($A_R$-Sense) triggers the ventricular escape interval, at the end of which a ventricular stimulation pulse is triggered if same is not inhibited by an occurrence of the ventricular sense event within the ventricular escape interval and outside the postatrial ventricular blanking time;

wherein the stimulation unit is actuated with regard to an interatrial conduction time such that an occurrence of the atrial sense event ($A_R$-Sense) triggers an interatrial conduction timer to create a predetermined $A_R$-$A_L$ time interval, at the end of which a stimulation pulse to the second atrium is triggered if the stimulation pulse to the second atrium is not inhibited; and wherein the stimulation unit is actuated such that the delivery of a stimulation pulse to the second atrium is suppressed when a ventricular sense event occurs during an upper tracking interval operating mode in which the cardiac pacemaker works at a predetermined maximum stimulation rate.

3. The pacemaker of claim 2, further comprising:
a further sensing unit for sense events of the second atrium, wherein the delivery of a stimulation pulse to the second atrium is suppressed when the further sensing unit produces a signal which is characteristic of a sense event ($A_L$-Sense) of the second atrium within the interatrial conduction time.

4. The pacemaker of claim 3, wherein:
the control unit is adapted to calculate the time spacing from a latest secured ventricular event to a next planned ventricular stimulation pulse.

5. The pacemaker of claim 4, wherein:
the control unit is adapted to compare the calculated time spacing to a predeterminable maximum value.

6. The pacemaker of claim 5, wherein:
the control unit is adapted to switch off interatrial synchronisation in dependence on the comparison between the calculated time spacing and the predetermined maximum value.

7. The pacemaker of claim 1, further comprising:
a further sensing unit for sense events of the second atrium, wherein the delivery of a stimulation pulse to the second atrium is suppressed when the further sensing unit produces a signal which is characteristic of a sense event ($A_L$-Sense) of the second atrium within the interatrial conduction time.

8. The pacemaker of claim 1, wherein:
the control unit is adapted to calculate the time spacing from a latest secured ventricular event to a next planned ventricular stimulation pulse.

9. The pacemaker of claim 7, wherein:
the control unit is adapted to calculate the time spacing from a latest secured ventricular event to a next planned ventricular stimulation pulse.

10. The pacemaker of claim 2, wherein:
the control unit is adapted to calculate the time spacing from a latest secured ventricular event to a next planned ventricular stimulation pulse.

11. The pacemaker of claim 8, wherein:
the control unit is adapted to compare the calculated time spacing to a predeterminable maximum value.

12. The pacemaker of claim 9, wherein:
the control unit is adapted to compare the calculated time spacing to a predeterminable maximum value.

13. The pacemaker of claim 10, wherein:
the control unit is adapted to compare the calculated time spacing to a predeterminable maximum value.

14. The pacemaker of claim 11, wherein:
the control unit is adapted to switch off interatrial synchronisation in dependence on the comparison between the calculated time spacing and the predetermined maximum value.

15. The pacemaker of claim 12, wherein:
the control unit is adapted to switch off interatrial synchronisation in dependence on the comparison between the calculated time spacing and the predetermined maximum value.

16. The pacemaker of claim 13, wherein:
the control unit is adapted to switch off interatrial synchronisation in dependence on the comparison between the calculated time spacing and the predetermined maximum value.

\* \* \* \* \*